(12) United States Patent
Richter et al.

(10) Patent No.: US 7,828,835 B2
(45) Date of Patent: *Nov. 9, 2010

(54) LONGITUDINALLY FLEXIBLE STENT

(75) Inventors: Jacob Richter, Ramat Hasharon (IL); Gregory Pinchasik, Herzlia (IL)

(73) Assignee: Medinol Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/864,389

(22) Filed: May 25, 2001

(65) Prior Publication Data

US 2002/0022876 A1 Feb. 21, 2002

Related U.S. Application Data

(63) Continuation-in-part of application No. 09/795,794, filed on Feb. 28, 2001, which is a continuation-in-part of application No. 09/516,753, filed on Mar. 1, 2000.

(60) Provisional application No. 60/202,723, filed on May 8, 2000.

(51) Int. Cl.
*A61F 2/06* (2006.01)
*A61M 29/00* (2006.01)

(52) U.S. Cl. ............... 623/1.15; 606/108; 606/198; 606/191; 606/194

(58) Field of Classification Search ............... 623/1.11, 623/1.12, 1.13, 1.14, 1.15, 1.16, 1.17, 1.18, 623/1.19, 1.2, 1.21, 1.22, 23.58, 23.59; 606/108, 606/191, 194, 195, 198

See application file for complete search history.

(56) References Cited

U.S. PATENT DOCUMENTS 4,733,665 A 3/1988 Palmaz
4,755,593 A 7/1988 Lauren
4,886,062 A 12/1989 Wiktor
5,037,377 A 8/1991 Alonso
5,133,732 A 7/1992 Wiktor (Continued)

FOREIGN PATENT DOCUMENTS

DE 43 03 181 A1 8/1994

(Continued)

OTHER PUBLICATIONS

Partial European Search Report.

(Continued)

*Primary Examiner*—Vy Q Bui
(74) *Attorney, Agent, or Firm*—Cadwalader Wickersham & Taft LLP

(57) ABSTRACT

An intravascular stent especially suited for implanting in curved arterial portions. The stent retains longitudinal flexibility after expansion. The stent is formed of intertwined meander patterns forming triangular cells. The triangular cells are adapted to provide radial support, and also to provide longitudinal flexibility after expansion. The triangular cells provide increased coverage of a vessel wall. The stent can have different portions adapted to optimize radial support or to optimize longitudinal flexibility. Loops in the stent are disposed and adapted to cooperate so that after expansion of said stent within a curved lumen, the stent is curved and cells on the outside of the curve open in length, but narrow in width whereas cells on the inside of the curve shorten in length but thicken in width to maintain a density of stent element area which much more constant than otherwise between the inside and the outside of the curve. As a result, when the stent is coated with a medicine the more constant density of stent elements results in an even dose being applied to the inside wall of the lumen, avoiding the possibility that a toxic dose be supplied at one area while a less than effective dose is applied to another area.

6 Claims, 14 Drawing Sheets

U.S. PATENT DOCUMENTS

| | | | |
|---|---|---|---|
| 5,510,077 A | 4/1996 | Dinh et al. | |
| 5,554,182 A | 9/1996 | Dinh et al. | |
| 5,571,166 A | 11/1996 | Dinh et al. | |
| 5,575,818 A | 11/1996 | Pinchuk | |
| 5,591,224 A | 1/1997 | Schwartz et al. | |
| 5,595,571 A | 1/1997 | Jaffe et al. | |
| 5,603,721 A | 2/1997 | Lau et al. | |
| 5,628,785 A | 5/1997 | Schwartz et al. | |
| 5,653,747 A | 8/1997 | Dereume | |
| 5,693,085 A | 12/1997 | Buirge et al. | |
| 5,695,516 A | 12/1997 | Fischell | |
| 5,697,971 A | 12/1997 | Fischell et al. | |
| 5,707,386 A | 1/1998 | Schnepp-Pesch et al. | |
| 5,720,777 A | 2/1998 | Jaffe et al. | |
| 5,733,303 A | 3/1998 | Israel et al. | |
| 5,800,507 A | 9/1998 | Schwartz | |
| 5,800,508 A | 9/1998 | Goicoechea et al. | 623/1 |
| 5,807,404 A | 9/1998 | Richter | |
| 5,827,321 A | 10/1998 | Roubin | |
| 5,836,964 A | 11/1998 | Richter et al. | |
| 5,837,313 A | 11/1998 | Ding | |
| 5,843,180 A | 12/1998 | Jaffe et al. | 623/2 |
| 5,843,181 A | 12/1998 | Jaffe et al. | |
| 5,849,034 A | 12/1998 | Schwartz | |
| 5,855,597 A | 1/1999 | Jayaraman | 623/1 |
| 5,855,600 A | 1/1999 | Alt | |
| 5,860,999 A | 1/1999 | Schnepp-Pesch et al. | |
| 5,865,723 A | 2/1999 | Love | |
| 5,895,407 A | 4/1999 | Jayaraman | |
| 5,913,895 A | 6/1999 | Burpee et al. | |
| 5,922,021 A | 7/1999 | Jang | 623/1 |
| 5,997,973 A | 12/1999 | Bianca, Jr. | |
| 6,013,091 A | 1/2000 | Ley et al. | 606/191 |
| 6,017,365 A | 1/2000 | Von Oepen | |
| 6,053,941 A | 4/2000 | Lindenberg et al. | |
| 6,120,847 A * | 9/2000 | Yang et al. | 424/422 |
| 6,132,461 A | 10/2000 | Thompson | 623/1.15 |
| 6,159,237 A | 12/2000 | Alt et al. | 623/1.11 |
| 6,162,245 A * | 12/2000 | Jayaraman | 623/1.15 |
| 6,179,868 B1 * | 1/2001 | Burpee et al. | 623/1.17 |
| 6,183,353 B1 | 2/2001 | Frantzen | 451/104 |
| 6,190,403 B1 * | 2/2001 | Fischell et al. | 623/1.16 |
| 6,190,406 B1 | 2/2001 | Duerig et al. | |
| 6,193,747 B1 * | 2/2001 | von Oepen | 623/1.15 |
| 6,197,048 B1 | 3/2001 | Richter | |
| 6,221,098 B1 | 4/2001 | Wilson et al. | 623/1.11 |
| 6,231,598 B1 * | 5/2001 | Berry et al. | 210/103 |
| 6,241,762 B1 | 6/2001 | Shanley | |
| 6,251,134 B1 | 6/2001 | Alt et al. | 623/1.16 |
| 6,299,604 B1 * | 10/2001 | Ragheb et al. | 604/265 |
| 6,348,065 B1 | 2/2002 | Brown et al. | 623/1.16 |
| 6,383,213 B2 | 5/2002 | Wilson et al. | 623/1.11 |
| 6,387,120 B2 | 5/2002 | Wilson et al. | 623/1.11 |
| 6,409,753 B1 | 6/2002 | Brown et al. | 623/1.15 |
| 6,416,538 B1 | 7/2002 | Ley et al. | 623/1.15 |
| 6,416,539 B1 | 7/2002 | Hassdenteufel | |
| 6,428,569 B1 | 8/2002 | Brown | 623/1.15 |
| 6,471,980 B2 | 10/2002 | Sirhan et al. | |
| 6,478,815 B1 | 11/2002 | Alt | 623/1.115 |
| 6,540,775 B1 | 4/2003 | Fischell | |
| 6,569,180 B1 | 5/2003 | Sirhan et al. | |
| 6,602,281 B1 | 8/2003 | Klein | |
| 6,602,282 B1 | 8/2003 | Yan | |
| 6,605,107 B1 | 8/2003 | Klein | |
| 6,648,911 B1 | 11/2003 | Sirhan et al. | |
| 6,652,573 B2 | 11/2003 | Von Oepen | |
| 6,776,793 B2 * | 8/2004 | Brown et al. | 623/1.15 |
| 6,790,227 B2 | 9/2004 | Burgermeister | |
| 6,955,686 B2 | 10/2005 | Majercak et al. | |
| 2001/0056298 A1 | 12/2001 | Brown et al. | 623/1.16 |
| 2002/0007212 A1 | 1/2002 | Brown et al. | 623/1.16 |
| 2002/0055770 A1 | 5/2002 | Doran et al. | 623/1.15 |
| 2002/0103529 A1 | 8/2002 | Pinchasik et al. | 623/1.15 |
| 2002/0116049 A1 | 8/2002 | Girton et al. | 623/1.15 |
| 2002/0138136 A1 | 9/2002 | Chandresekaran et al. | 623/1.34 |
| 2002/0177893 A1 | 11/2002 | Brown et al. | 623/1.16 |
| 2004/0088043 A1 | 5/2004 | Klein | |
| 2005/0273157 A1 | 12/2005 | Pinchasik | |

FOREIGN PATENT DOCUMENTS

| | | |
|---|---|---|
| DE | 195 12 066 | 11/1996 |
| DE | 29708879 U1 | 7/1999 |
| DE | 197 53 123 A | 8/1999 |
| DE | 197 53 123 A1 | 8/1999 |
| DE | 199 00 411 A | 7/2000 |
| DE | 199 00 411 A1 | 7/2000 |
| DE | 19957063 | 8/2001 |
| DE | 20108765 U1 | 10/2001 |
| DE | 20108764 U | 11/2001 |
| EP | 0 623 354 A1 | 11/1994 |
| EP | 0 830 853 | 3/1998 |
| EP | 0 830 853 A1 | 3/1998 |
| EP | 0 958 794 A2 | 12/1999 |
| EP | 0 958 794 A3 | 12/1999 |
| EP | 0 970 664 A2 | 1/2000 |
| EP | 0876216 | 4/2000 |
| EP | 1 020 166 A1 | 7/2000 |
| EP | 1 129 673 A2 | 9/2001 |
| FR | 2 758 253 A1 | 7/1998 |
| FR | 2758253 | 7/1998 |
| NZ | 280547 | 9/1998 |
| NZ | 285241 | 3/1999 |
| NZ | 331532 | 1/2000 |
| WO | WO 96/26689 | 9/1996 |
| WO | WO 97/07889 | 3/1997 |
| WO | WO 97/32544 | 9/1997 |
| WO | WO 98/35634 | 8/1998 |
| WO | WO 98 35634 | 8/1998 |
| WO | WO 99/15108 | 4/1999 |
| WO | 99/39660 | 8/1999 |
| WO | WO 99/44543 | 9/1999 |
| WO | 99/62431 | 12/1999 |
| WO | 00 30563 A | 6/2000 |
| WO | 00/30563 A | 6/2000 |
| WO | WO 00/30563 | 6/2000 |
| WO | 00/49971 A | 8/2000 |
| WO | WO 02/060344 | 8/2002 |

OTHER PUBLICATIONS

Patent Act 1977: Search Report under Section 17.
Cancellation Proceeding against DE Patent No. 20108764.
Cancellation Proceeding against DE Patent No. 20108765.
Supplementary European Search Report
European Search Report from corresponding EP Publication No. 1 908 437 dated Feb. 4, 2010, 5 pages.
Office Actions and Responses to Office Actions of related U.S. Appl. No. 10/236,144 issued as US Patent No. 7,621,947: Notice of Allowance dated Jul. 13, 2009; Terminal Disclaimer filed, dated May 8, 2009; Amendment and Response to Non-Final Office Action with Extension of Time dated Feb. 2, 2009; Non-Final Rejection dated Oct. 2, 2008.
Office Actions and Responses to Office Actions of related U.S. Appl. No. 10/619,837: Notice of Allowance dated Oct. 13, 2009; Request for Continued Examination (RCE); Amendment and Response to Final Rejection dated Jul. 29, 2009; Final Rejection dated Apr. 29, 2009; Amendment and Response to Non-Final Rejection with Extension of Time dated Dec. 16, 2008.
Office Actions and Responses to Office Actions of related U.S. Appl. No. 10/660,883: Notice of Abandonment dated Apr. 28, 2009; Advisory Action dated Jan. 30, 2009; Amendment and Response to Final Rejection with Extension of Time dated Jan. 7, 2009.
Office Actions and Responses to Office Actions of related U.S. Appl. No. 10/757,805: Amendment after Notice of Allowance dated Mar.

16, 2010; Notice of Allowance dated Dec. 17, 2009; Amendment and Response to Final Rejection with Request for Continued Examination (RCE) dated Jun. 29, 2009; Final Rejection dated Apr. 16, 2009; Amendment and Response to Non-Final Rejection with Extension of Time dated Jan. 14, 2009.

Office Actions and Responses to Office Actions of related U.S. Appl. No. 11/395,751: Amendment and Response to Supplemental Non-Final Rejection dated Feb. 22, 2010; Supplemental Non-Final Rejection dated Nov. 20, 2009; Non-Final Rejection dated Oct. 20, 2009; Pre-Appeal Conference Decision dated Aug. 5, 2009; Notice of Appeal with Extension of Time and Pre-Brief Conference Request dated May 14, 2009;Final Rejection dated Dec. 15, 2008.

Office Actions and Responses to Office Actions of related U.S. Appl. No. 12/042,470: Supplemental Amendment and Response to Non-Final Rejection dated Apr. 26, 2010; Correspondence dated Mar. 1, 2010 confirming that the Aug. 19, 2009 Restriction Requirement was sent in error by the Examiner; Non-Final Rejection/ Requirement for Restriction/Election dated Aug. 19, 2009; Response to Election/Restriction Requirement dated Apr. 20, 2009; Requirement for Restriction/Election dated Mar. 20, 2009; Amendment and Response to Non-Final Rejection dated Dec. 17, 2008; Supplemental Amendment and Response to Non-Final Rejection dated Dec. 17, 2008; Non-Final Rejection dated Sep. 17, 2008.

Office Actions and Responses to Office Actions of related U.S. Appl. No. 09/516,753, issued as U.S. Pat. No. 7,141,062: Notice of Allowance mailed Jul. 28, 2006, Amendment and Response to Final Office Action dated Jun. 8, 2006. Final Office Action dated Dec. 8, 2005. Amendment and Response to Non-Final Office Action dated Aug. 15, 2005. Non-Final Office Action dated Mar. 15, 2005. Response to Election Requirement dated Nov. 2, 2004. Election Requirement dated Aug. 11, 2004. Amendment and Response to Final Office Action dated May 13, 2004. Final Office Action dated Feb. 6, 2004. Amendment and Response to Non-Final Office Action dated Nov. 13, 2003. Non-Final Office Action dated Aug. 13, 2003. Amendment and Response to Final Office Action dated Jun. 2, 2003. Final Office Action dated Dec. 3, 2002. Amendment and Response to Non-Final Office Action dated Jul. 26, 2002. Non-Final Office Action dated Jan. 30, 2002.

Office Actions, Responses to Office Actions and Notice of Allowance of related U.S. Appl. No. 09/795,794, issued as U.S. Pat. No. 6,709,453: Non-Final Office Action dated Dec. 20, 2001. Response to Office Action dated Jun. 19, 2002. Supplemental Amendment dated Aug. 5, 2002. Final Office Action dated Jan. 30, 2003. Amendment and Response to Final Office Action dated May 1, 2003. Non-Final Office Action dated Jul. 15, 2003, Amendment and Response to Final Office Action dated Sep. 11, 2003. Supplemental Response dated Sep. 17, 2003. Supplemental Response dated Sep. 22, 2003. Notice of Allowance dated Sep. 24, 2003.

Office Actions, Responses to Office Actions and Notice of Allowance of related U.S. Appl. No. 09/864,160, issued as U.S. Pat. No. 6,723,119: Non-Final Office Action dated Jan. 29, 2002. Amendment and Response to Non-Final Office Action dated Jun. 26, 2002. Supplemental Response dated Aug. 5, 2002. Final Office Action dated Dec. 3, 2002. Notice of Appeal dated Jun. 3, 2002. Notice of Allowance dated Sep. 26, 2003. Response After Final dated Sep. 11, 2003, Supplemental Response After Final dated Sep. 17, 2003.

Office Actions and Responses to Office Actions of related U.S. Appl. No. 10/040,789, now abandoned: Notice of Abandonment dated Jun. 6, 2005, Response to Non-Compliant Amendment dated Apr. 21, 2005. Notice of Non-Compliant Amendment dated Mar. 21, 2005.

Amendment and Response to Non-Final Office Action dated Feb. 24, 2005. Non-Final Office Action dated Aug. 25, 2004. Preliminary Amendment dated Jan. 16, 2003.

Office Actions and Responses to Office Actions of related U.S. Appl. No. 10/236,144: Amendment and Response to Final Office Action dated Jan. 9, 2008, Non-Final Office Action dated Sep. 21, 2007. Amendment and Responsse to Final Office Action dated Jun. 26, 2007, Final Office Action dated Feb. 26, 2007. Amendment and Response Non-Final Office Action dated Aug. 7, 2006. Non-Final Office Action dated Feb. 8, 2006. Response to Election Requirement dated Nov. 17, 2005. Election Requirement dated Sep. 21, 2005.

Office Actions and Responses to Office Actions of related U.S. Appl. No. 10/619,837: Amendment and Response to Non-Final Office Action and Terminal Disclaimer dated Feb. 4, 2008. Non-Final Office Action dated Oct. 4, 2007. Response to Election Requirement dated Feb. 5, 2007. Election Requirement dated Jan. 4, 2007.

Office Actions and Responses to Office Actions of related U.S. Appl. No. 10/660,883: Amendment and Response to Non-Final Office Action dated Jan. 25, 2008. Non-Final Office Action dated Oct. 25, 2007.

Office Actions and Responses to Office Actions of related U.S. Appl. No. 11/395,751: Amendment and Response to Election Requirement dated Dec. 10, 2007. Requirement for Restriction/Election dated Nov. 8, 2007. Amendment and Response to Non-Final Office Action dated Jul. 11, 2007. Non-Final Office Action dated Apr. 11, 2007.

Office Actions and Responses to Office Actions of related U.S. Appl. No. 10/236,144: Final Office Action dated May 23, 2008.

Office Actions and Responses to Office Actions of related U.S. Appl. No. 10/660,883: Requirement for Restriction/Election dated Apr. 28, 2008, Amendment and Response to Election Requirement dated May 28, 2008.

Office Actions and Responses to Office Actions of related U.S. Appl. No. 10/757,805: Requirement for Restriction/Election dated Apr. 7, 2008, Amendment and Response to Election Requirement dated May 7, 2008.

Office Actions and Responses to Office Actions of related U.S. Appl. No. 11/395,751: Non-Final Office Action dated Apr. 23, 2008.

Response to Office Action of related U.S. Appl. No.: 10/236,144, Amendment and Reponse to Final Rejection and Request for Contiued Examination dated Aug. 22, 2008.

Office Action of related U.S. Appl. No. 10/619,387, Non-Final Office Action Mailed Jul. 23, 2008.

Office Action of related U.S. Appl. No. 10/660,883, Final Rejection Office Action Mailed Aug. 7, 2008.

Office Action of related U.S. Appl. No. 10/757,805, Non-Final Office Action Mailed Aug. 14, 2008.

Response to Office Action of related U.S. Appl. No. 11/395,751, Amendment and Reponse to Non-Final Rejection and Extension of Time dated Aug. 20, 2008.

Office Actions and Reponses to Office Actions of related U.S. Appl. No. 11/395,751: Final Rejection dated Jul. 14, 2010.

Office Actions and Reponses to Office Actions of related U.S. Appl. No. 12/042,470: Response to Non-Final Rejection dated Aug. 10, 2010; and Non-Final Rejection dated May 10, 2010.

Two European Search Reports.

PCT Search Reports.

Singapore Examination Report.

New Zealand Examination Report.

German Office Action.

* cited by examiner

US 7,828,835 B2

LONGITUDINALLY FLEXIBLE STENT

RELATED APPLICATIONS

This application is a continuation-in-part of Ser. No. 09/795,794 filed Feb. 28, 2001, which is a continuation-in-part of Ser. No. 09/516,753 filed Mar. 1, 2000 and which also claims the priority of Provisional Application No. 60/202,723, filed May 8, 2000.

FIELD OF THE INVENTION

The present invention relates generally to stents, which are endoprostheses implanted into vessels within the body, such as blood vessels, to support and hold open the vessels, or to secure and support other endoprostheses in the vessels. In particular, the present invention relates to a stent which is longitudinally flexible before and after expansion.

BACKGROUND OF THE INVENTION

Various stents are known in the art. Typically stents are generally tubular in shape, and are expandable from a relatively small, unexpanded diameter to a larger, expanded diameter. For implantation, the stent is typically mounted on the end of a catheter, with the stent being held on the catheter at its relatively small, unexpanded diameter. By the catheter, the unexpanded stent is directed through the lumen to the intended implantation site. Once the stent is at the intended implantation site, it is expanded, typically either by an internal force, for example by inflating a balloon on the inside of the stent, or by allowing the stent to self-expand, for example by removing a sleeve from around a self-expanding stent, allowing the stent to expand outwardly. In either case, the expanded stent resists the tendency of the vessel to narrow, thereby maintaining the vessel's patency.

U.S. Pat. No. 5,733,303 to Israel et al. ("'303"), which is expressly incorporated by reference, shows a unique stent formed of a tube having a patterned shape which has first and second meander patterns having axes extending in first and second directions. The second meander patterns are intertwined with the first meander patterns to form flexible cells. Stents such as this one are very flexible in their unexpanded state such that they can be tracked easily down tortuous lumens. Upon expansion, these stents provide excellent radial support, stability, and coverage of the vessel wall. These stents are also conformable, in that they adapt to the shape of the vessel wall during implantation. It is readily apparent that, by nature, when the stent shown, for example, in FIG. 8 thereof is expanded in a curved lumen, cells on the outside of the curve open in length, but narrow in width whereas cells on the inside of the curve shorten in length but thicken in width to maintain a density of stent element area which much more constant than otherwise between the inside and the outside of the curve.

One feature of stents with a cellular mesh design such as this one, however, is that they have limited longitudinal flexibility after expansion, which may be a disadvantage in particular applications. This limited longitudinal flexibility may cause stress points at the end of the stent and along the length of the stent. Conventional mesh stents like that shown in U.S. Pat. No. 4,733,665 may simply lack longitudinal flexibility, which is illustrated by FIG. 1, a schematic diagram of a conventional stent 202 in a curved vessel 204.

To implant a stent, it maybe delivered to a desired site by a balloon catheter when the stent is in an unexpanded state. The balloon catheter is then inflated to expand the stent, affixing the stent into place. Due to the high inflation pressures of the balloon—up to 20 atm—the balloon causes the curved vessel 204 and even a longitudinally flexible stent to straighten when it is inflated. If the stent, because of the configuration of its mesh is or becomes relatively rigid after expansion, then the stent remains or tends to remain in the same or substantially the same shape after deflation of the balloon. However, the artery attempts to return to its natural curve (indicated by dashed lines) in FIG. 1 with reference to a conventional mesh stent. The mismatch between the natural curve of the artery and the straightened section of the artery with a stent may cause points of stress concentration 206 at the ends of the stent and stress along the entire stent length. The coronary vasculature can impose additional stress on stents because the coronary vasculature moves relatively significant amounts with each heartbeat. For illustration purposes, the difference between the curve of the vessel and the straightened stent has been exaggerated in FIG. 1.

U.S. Pat. No. 5,807,404 to Richter, which is expressly incorporated by reference, shows another stent which is especially suited for implantation into curved arterial portions or osteal regions. This stent can include sections adjacent the end of the stent with greater bending flexibility than the remaining axial length of the stent. While this modification at the end of the stent alleviates the stress at the end points, it does not eliminate the stress along the entire length of the stent.

Various stents are known that retain longitudinal flexibility after expansion. For example, U.S. Pat. Nos. 4,886,062 and 5,133,732 to Wiktor ("the Wiktor '062 and '732 patents") show various stents formed of wire wherein the wire is initially formed into a band of zig-zags forming a serpentine pattern, and then the zig-zag band is coiled into a helical stent. The stents are expanded by an internal force, for example by inflating a balloon.

The coiled zig-zag stents that are illustrated in FIGS. 1 through 6 of the Wiktor '062 and '732 patents are longitudinally flexible both in the expanded and unexpanded condition such that they can be tracked easily down tortuous lumens and such that they conform relatively closely to the compliance of the vessel after deployment. While these stents are flexible, they also have relatively unstable support after expansion. Furthermore, these stents leave large portions of the vessel wall uncovered, allowing tissue and plaque prolapse into the lumen of the vessel.

Thus, it is desired to have a stent which exhibits longitudinal flexibility before expansion such that it can easily be tracked down tortuous lumens and longitudinal flexibility after expansion such that it can comply with the vessel's natural flexibility and curvature while still providing continuous, stable coverage of a vessel wall that will minimize tissue sag into the lumen.

SUMMARY OF THE INVENTION

Accordingly, an object of the invention is to provide a stent that is longitudinally flexible before expansion so that it can easily be tracked down tortuous vessels and remains longitudinally flexible after expansion such that it will substantially eliminate any stress points by complying with the vessel's flexibility and assuming the natural curve of the vessel.

Another object of the present invention is to provide a stent that is longitudinally flexible after delivery such that it flexes during the cycles of the heartbeat to reduce cyclic stress at the ends of the stent and along the stent.

Another object of the present invention is to provide a stent with a closed cell pattern such that it provides good coverage and support to a vessel wall after expansion.

Other advantages of the present invention will be apparent to those skilled in the art.

In accordance with these objects, the stent of the present invention is formed to be a tube having a patterned shape which has first and second meander patterns having axes extending in first and second direction wherein the second meander patterns are intertwined with the first meander patterns.

In accordance with one embodiment of the invention, the intertwined meander patterns form cells which have three points at which the first and second meander patterns meet each other, and which in this sense could be called triangular cells. These three cornered or triangular cells are flexible about the longitudinal axis of the stent after expansion. These triangular cells provide comparable scaffolding and radial strength to that of cells formed by intertwined meander patterns which have four points at which the first and second patterns meet each other, and which in this sense could be called square cells.

In another embodiment of the invention, bands of cells are provided along the length of a stent. The bands of cells alternate between cells adapted predominantly to enhance radial support with cells that are adapted predominantly to enhance longitudinal flexibility after expansion.

In another embodiment of the invention, the first meander patterns are adapted to prevent any "flaring out" of loops of the first meander patterns during delivery of the stent.

A stent according to the invention retains the longitudinal flexibility associated with the '303 cellular stent in its unexpanded state, and has increased longitudinal flexibility in the expanded state. The stent does so without sacrificing scaffolding—i.e. coverage of the vessel wall—or radial support.

In this and other embodiments, cells formed by the meander patterns are such that, when the expanded stent is bent while inside a lumen, the cells on the outside of the curve open in length, but narrow in width whereas the cells on the inside of the curve shorten in length but thicken in width so that the area of the cell, and the density of the struts, remains much more constant than otherwise. This results in maintaining a more constant density of stent elements in contact with the lumen, irrespective of location on the inside or outside of a curved section. In turn, when the stent is coated with a medicine, a more even dose is applied to the inside wall of the lumen, avoiding the possibility that a toxic dose be supplied at one area while a less than effective dose is applied to another area.

DETAILED DESCRIPTION OF THE INVENTION

Figure 1:
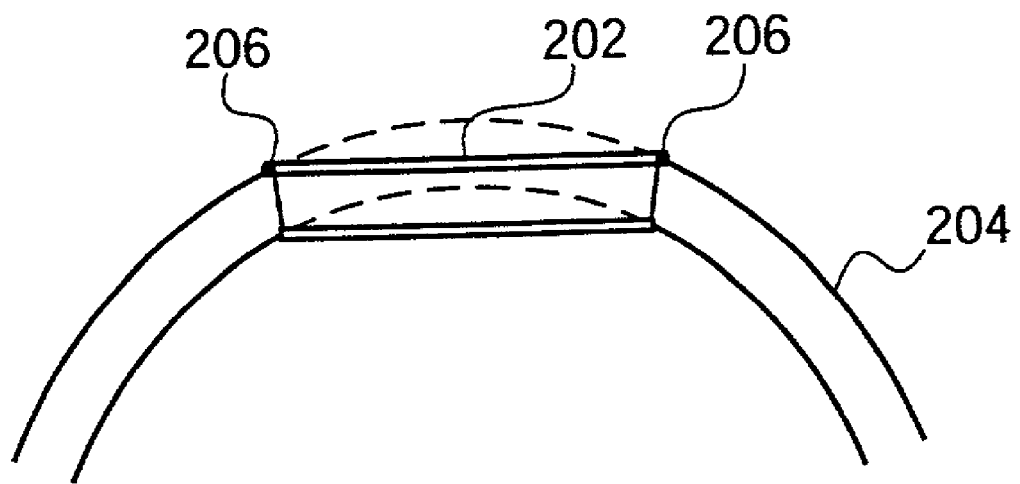
FIG. 1 shows a schematic diagram of a conventional rigid stent deployed in a curved lumen.
Figure 2:
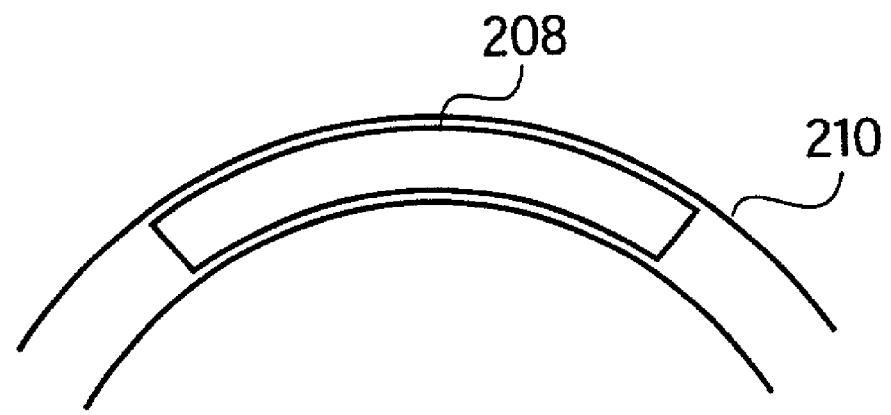
FIG. 2 shows a schematic diagram of a stent of the present invention deployed in a curved lumen.

FIG. 2 shows a schematic diagram of a longitudinally flexible stent 208 of the present invention. The stent 208 may be delivered to a curved vessel 210 by a balloon catheter, and implanted in the artery by inflating the balloon. As described before, the balloon causes the artery to straighten upon inflation of the balloon. However, upon deflation of the balloon, the stent 208 assumes the natural curve of the vessel 210 because it is and remains longitudinally flexible after expansion. This reduces any potential stress points at the ends of the stent and along the length of the stent. Furthermore, because the stent is longitudinally flexible after expansion, the stent will flex longitudinally with the vessel during the cycles caused by a heartbeat. This also reduces any cyclic stress at the ends of the stent and along the length of the stent.

Figure 3:
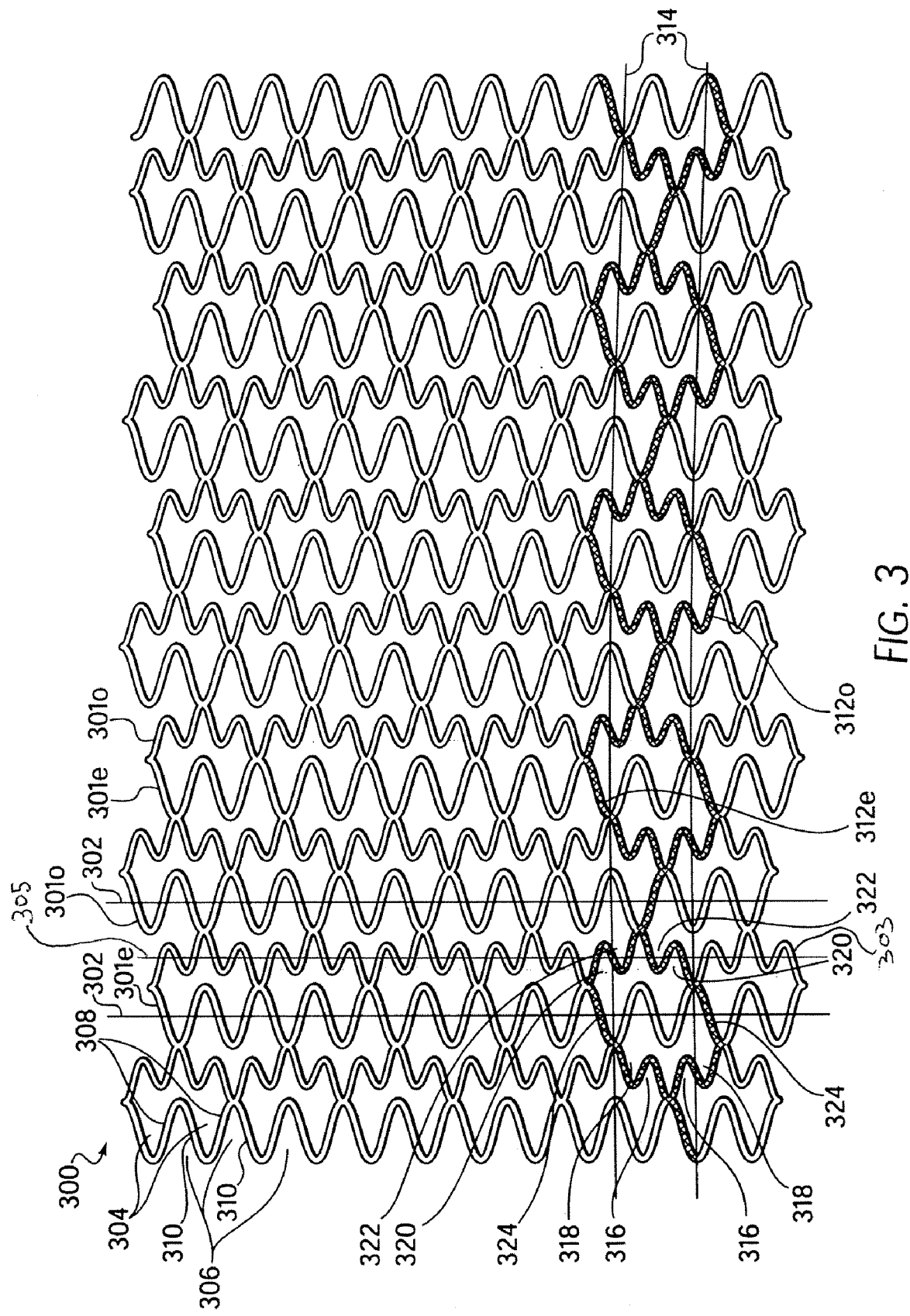
FIG. 3 shows a pattern for a stent made in accordance with the present invention.

FIG. 3 shows a pattern of a stent according to the present invention. This pattern may be constructed of known materials, and for example stainless steel, but it is particularly suitable to be constructed from NiTi. The pattern can be formed by etching a flat sheet of NiTi into the pattern shown. The flat sheet is formed into a stent by rolling the etched sheet into a tubular shape, and welding the edges of the sheet together to form a tubular stent. The details of this method of forming the stent, which has certain advantages, are disclosed in U.S. Pat. Nos. 5,836,964 and 5,997,973, which are hereby expressly incorporated by reference. Other methods known to those of skill in the art such as laser cutting a tube or etching a tube may also be used to construct a stent which uses the present invention. After formation into a tubular shape, a NiTi stent is heat treated, as known by those skilled in the art, to take advantage of the shape memory characteristics of NiTi and its superelasticity.

The pattern 300 is formed from a plurality of each of two orthogonal meander patterns which patterns are intertwined with each other. The term "meander pattern" is taken herein to describe a periodic pattern about a center line and "orthogonal meander patterns" are patterns whose center lines are orthogonal to each other.

A meander pattern 301 is a vertical sinusoid having a vertical center line 302. It will be recognized that this is not a perfect sinusoid, but only an approximation thereof. Thus, as used herein, the term sinusoid refers to a periodic pattern which varies positively and negatively symmetrically about an axis; it need not be an exact sine function. A meander pattern 301 has two loops 304 and 306 per period wherein loops 304 open to the right while loops 306 open to the left. Loops 304 and 306 share common members 308 and 310, where member 308 joins one loop 304 to its following loop 306 and member 308 joins one loop 306 to its following loop 304. The vertical sinusoid of meander pattern 301 has a first frequency.

A meander pattern 312 (two of which have been shaded for reference) is a horizontal pattern having a horizontal center line 314. A horizontal meander pattern 312 also has loops labeled 316, 318, 320, 322, and between the loops of a period is a section labeled 324. Looked at another way, these loops are part of a vertical sinusoid 303 which has a higher frequency than that of the meander patterns 301. Vertical sinusoids 301 alternate with vertical sinusoids 303. Vertical sinusoids 303 have a second frequency higher than the first frequency of the vertical meander patterns, i.e., sinusoids 301.

Vertical meander pattern 301 is provided in odd and even (o and e) versions which are 180° out of phase with each other. Thus, each left opening loop 306 of meander pattern 301o faces a right opening loop 304 of meander pattern 301e and a right opening loop 304 of meander pattern 301o faces a left opening loop 306 of meander pattern 301e.

The horizontal meander pattern 312 is also provided in odd and even forms. The straight sections 324 of the horizontal meander pattern 312e intersect with every third common member 310 of the even vertical meander pattern 301e. The straight sections 324 of the horizontal meander pattern 312o also intersect with every third common member 310 of the odd vertical meander pattern 301. Viewed as vertical sinusoids 303, alternating sinusoids 303 are intermittently coupled to the meander patterns 301. For example, between points 315 and 317, where vertical pattern 303 is coupled to vertical pattern 301e, there are two loops 306 and one loop 304 of vertical pattern 301e and three loops 319 and two loops 321 of vertical pattern 303. This corresponds to two cycles of pattern 301e and 3 cycles of pattern 303. Similarly, between two points of coupling between vertical pattern 301o and vertical pattern 303 are two loops 304 and one loop 306, again making two cycles. There will be three loops 321 and two loops 319, again equal to three cycles of pattern 303.

Since this embodiment of the stent is made of NiTi, and it is reboundable, it typically will be self-expanding. Upon expansion of the stent, the loops of the vertical meander patterns 301 open up in the vertical direction. This causes them to shorten in the horizontal direction. The loops in the horizontal meander pattern 312 open up both in the vertical direction and the horizontal direction, compensating for the shortening of the loops of the vertical meander patterns.

Figure 7:
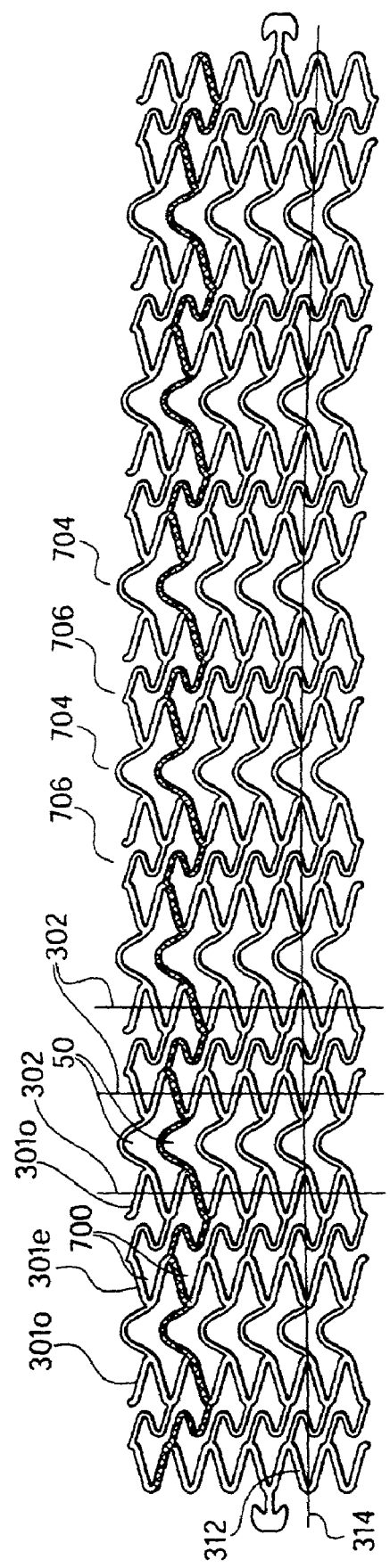
FIG. 7 shows a pattern for a stent made in accordance with the present invention.
Figure 14:
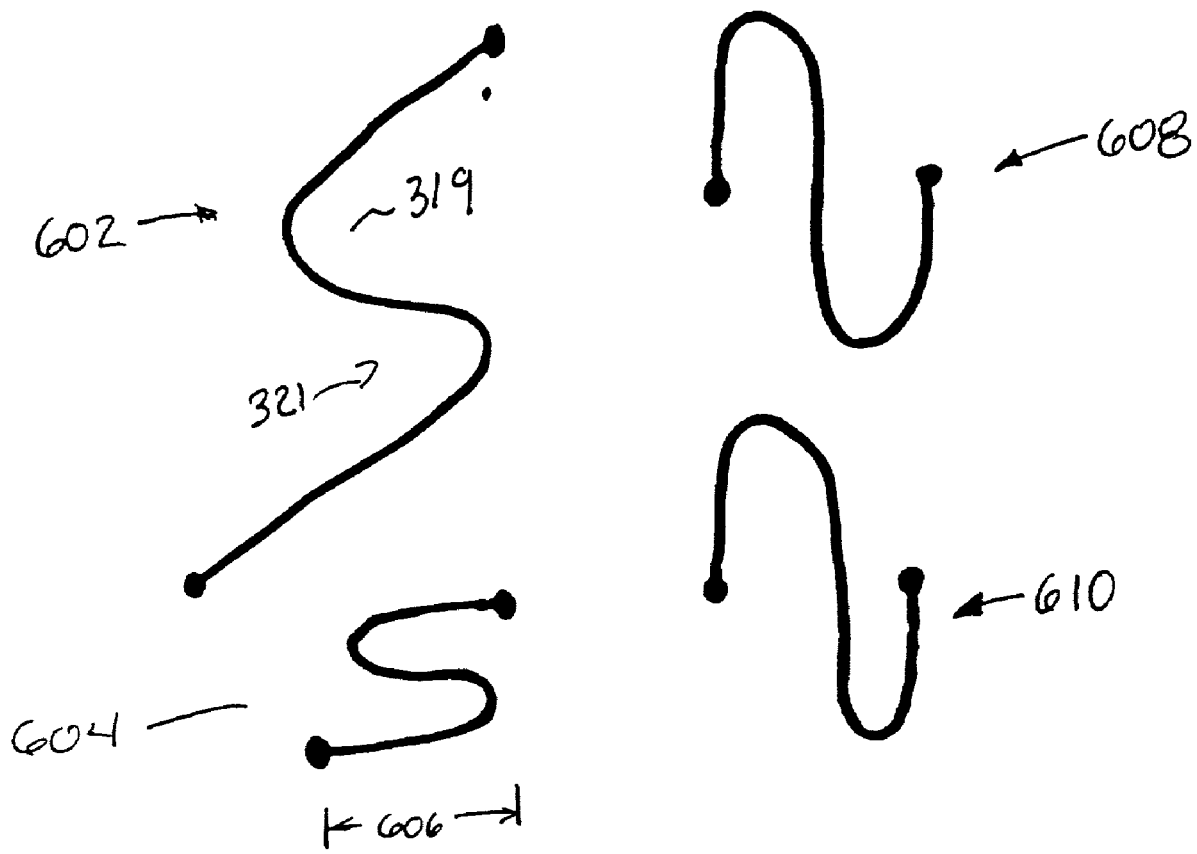
FIG. 14 shows the expansion of a portion of a horizontal meander pattern built according to the principles of the invention.

It should be noted that the loops of the horizontal meander pattern 312, which are the loops of the vertical pattern 303 in the present invention avoids foreshortening in a self-expanding stent in a particularly effective manner. A self-expanding stent formed of a shape-memory alloy must be compressed from an expanded position to a compressed position for delivery. As shown in FIG. 7, because of the configuration of the loops 319 and 321 of the horizontal meander pattern 312, when the stent is compressed from an expanded position 602 to a compressed position 604, the length 606 of the horizontal meander pattern (width of the vertical pattern 330) naturally shrinks. Consequently, when the stent expands, the loops 319 and 321 elongate and compensate for the shortening of the vertical meander patterns 301e and 301o as the vertical meander patterns 301e and 301o expand. In contrast, a horizontal meander pattern with such shapes as N-shapes will not naturally shrink longitudinally when compressed from an expanded position 608 to a compressed position 610, as illustrated in FIG. 14.

A stent formed from the pattern of FIG. 3 and made of NiTi is particularly well suited for use in the carotid artery or other lumens subject to an outside pressure. One reason is that because the stent is formed of NiTi, it is reboundable, which is a desirable property for stents placed in the carotid artery. The other reason is that the stent of FIG. 3 offers excellent scaffolding, which is particularly important in the carotid artery. Scaffolding is especially important in the carotid artery because dislodged particles in the artery may embolize and cause a stroke.

Figure 4:
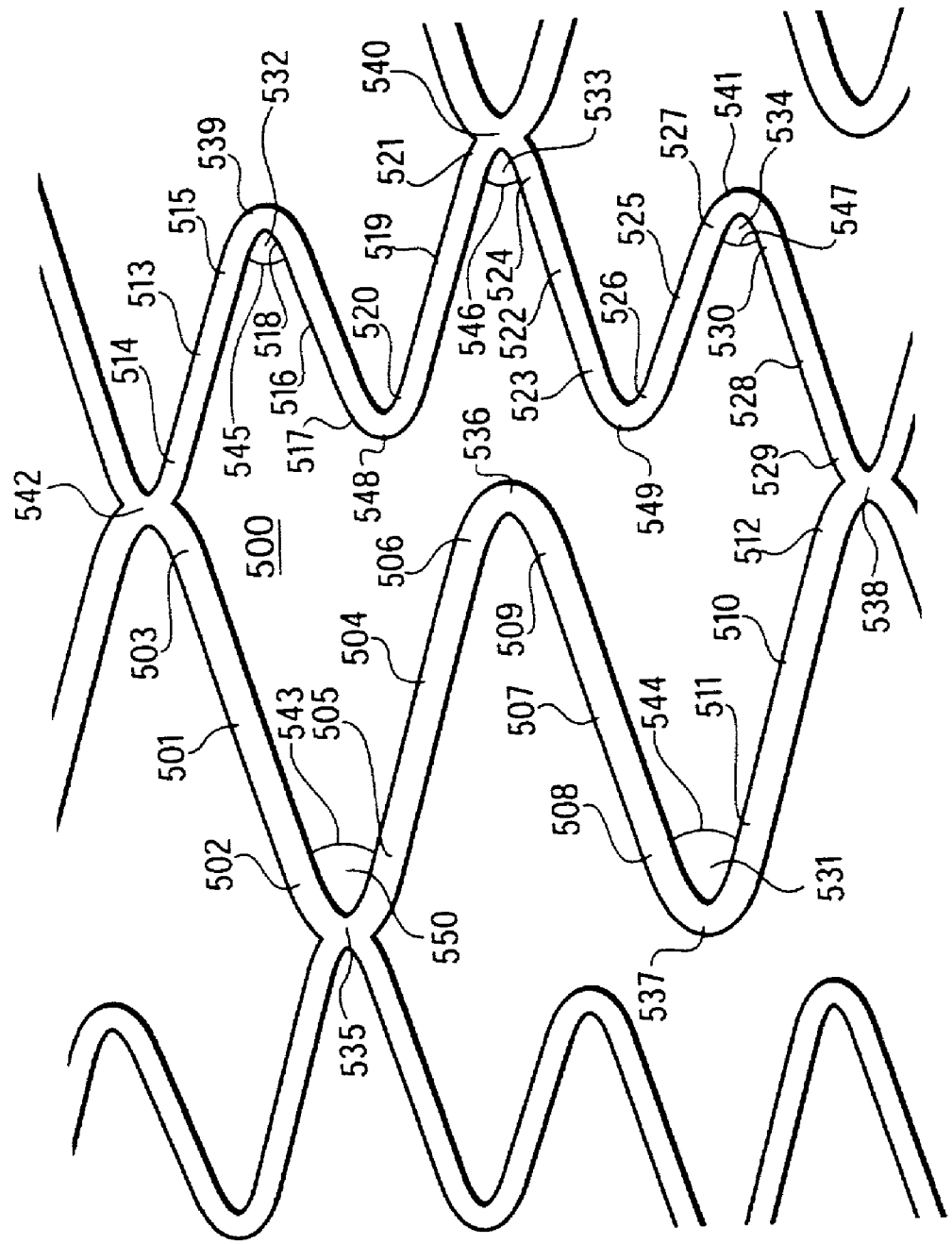
FIG. 4 shows an enlarged view of one cell of the pattern of FIG. 3.

FIG. 4 is an expanded view of one flexible cell 500 of the pattern of FIG. 3. Each flexible cell 500 includes: a first member 501 having a first end 502 and a second end 503; a second member 504 having a first end 505 and a second end 506; a third member 507 having a first end 508 and a second end 509; and a fourth member 510 having a first end 511 and a second end 512. The first end 502 of the first member 501 is joined to the first end 505 of the second member 504 by a first curved member 535 to form a first loop 550, the second end 506 of the second member 504 is joined to the second end 509 of the third member 508 by a second curved member 536, and the first end 508 of the third member 507 is joined to the first end 511 of the fourth member 510 by a third curved member 537 to form a second loop 531. The first loop 530 defines a first angle 543. The second loop 531 defines a second angle 544. Each cell 500 also includes a fifth member 513 having a first end 514 and a second end 515; a sixth member 516 having a first end 517 and a second end 518; a seventh member 519 having a first end 520 and a second end 521; an eighth member 522 having a first end 523 and a second end 524; a ninth member 525 having a first end 526 and a second end 527; and a tenth member having a first end 529 and a second end 530. The first end 514 of the fifth member 513 is joined to the second end 503 of the first member 501 at second junction point 542, the second end 515 of the fifth member 513 is joined to the second end 518 of the sixth member by a curved member 539 to form a third loop 532, the first end 517 of the sixth member 516 is joined to the first end 520 of the seventh member 519 by a fifth curved member 548, the second end 521 of the seventh member 519 is joined to the second end 524 of the eighth member 522 at third junction point 540 to form a fourth loop 533, the first end 523 of the eighth member 522 is joined to the first end 526 of the ninth member 525 by a sixth curved member 549, the second end 526 of the ninth member 525 is joined to the second end 530 of the tenth member 528 by a seventh curved member 541 to form a fifth loop 534, and the first end 529 of the tenth member 528 is joined to the second end 512 of the fourth member 510. The third loop 532 defines a third angle 545. The fourth loop 533 defines a fourth angle 546. The fifth loop 534 defines a fifth angle 547.

In the embodiment shown in FIG. 4, the first member 501, the third member 507, the sixth member 516, the eighth member 522, and the tenth member 528 have substantially the same angular orientation to the longitudinal axis of the stent and the second member 504, the fourth member 510, the fifth member 513, the seventh member 519, and the ninth member 512 have substantially the same angular orientation to the longitudinal axis of the stent. In the embodiment shown in FIG. 4, the lengths of the first, second, third and fourth members 501, 504, 507, 510 are substantially equal. The lengths of the fifth, sixth, seventh, eighth, ninth and tenth members 513, 516, 519, 522, 525, 528 are also substantially equal. Other embodiments where lengths of individual members are tailored for specific applications, materials of construction or methods of delivery are also possible, and may be preferable for them. It can be seen that each cell includes two cycles of the lower frequency vertical pattern and three cycles of the higher frequency vertical pattern.

The first, second, third, and fourth members 501, 504, 507, 510 may have a width that is greater than the width of the fifth, sixth, seventh, eighth, ninth, and tenth members 513, 516, 519, 522, 525, 528 in that cell. The differing widths of the first, second, third, and fourth members and the fifth, sixth, seventh, eighth, ninth, and tenth members with respect to each other contribute to the overall flexibility and resistance to radial compression of the cell. The widths of the various members can be tailored for specific applications. For example, the ratio of width may be approximately 50-70%. The fifth, sixth, seventh, eighth, ninth, and tenth members may be optimized predominantly to enable longitudinal flexibility, both before and after expansion, while the first, second, third, and fourth members may be optimized predominantly to enable sufficient resistance to radial compression to hold a vessel open. Although specific members may be optimized to predominantly enable a desired characteristic, all the portions of the cell interactively cooperate and contribute to the characteristics of the stent.

Figure 5:
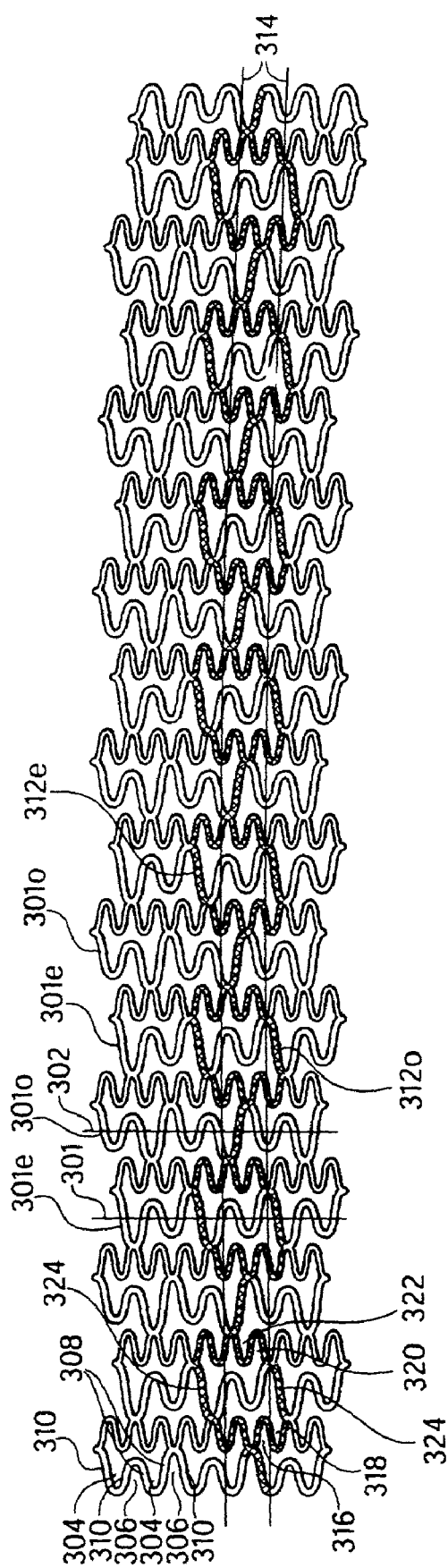
FIG. 5 shows a pattern for a stent made in accordance with the present invention.
Figure 6:
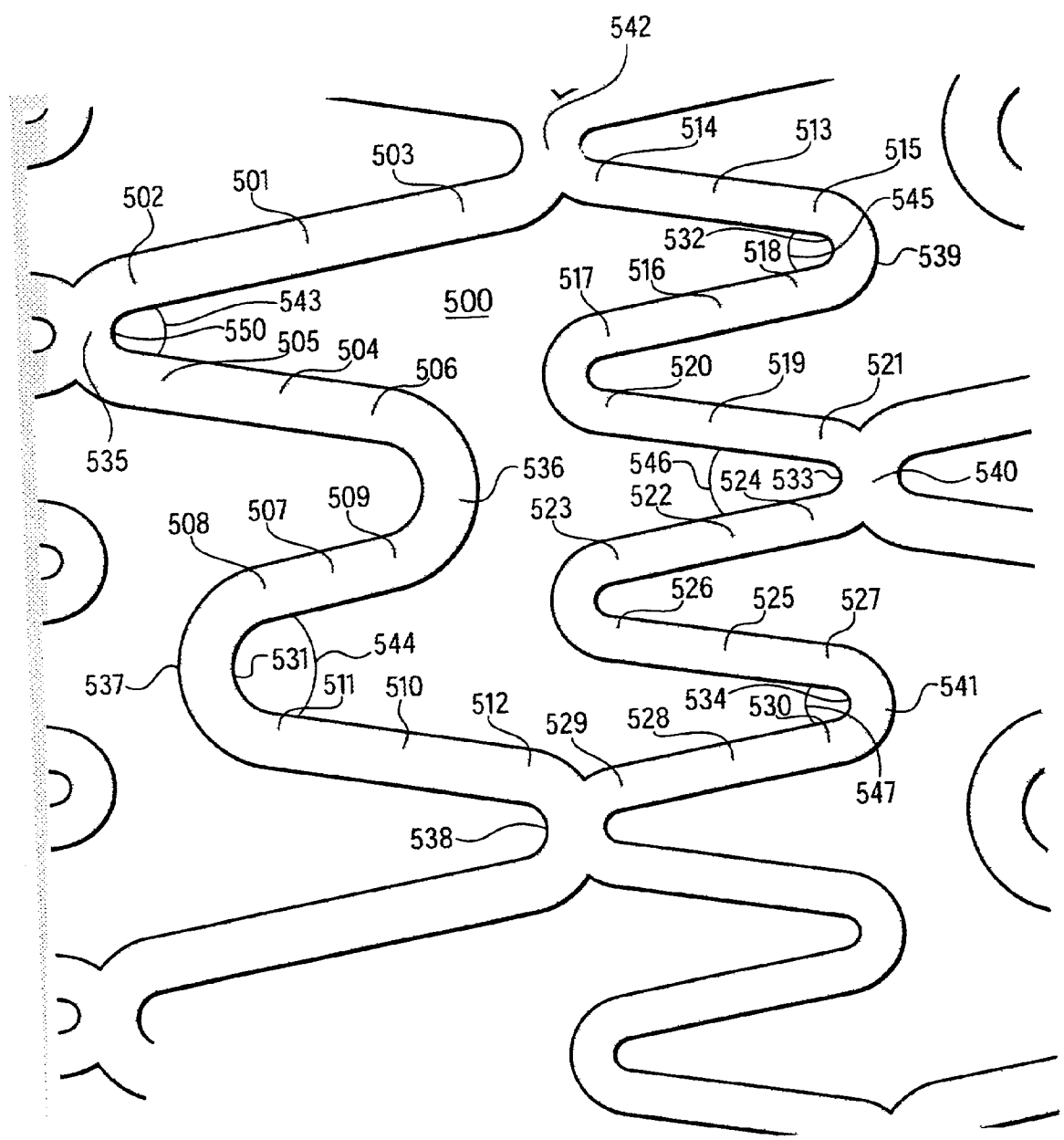
FIG. 6 shows an enlarged view of one cell of the pattern of FIG. 5.

FIGS. 5 and 6 show a pattern and an expanded view of one cell of an embodiment of the present invention which is specially adapted for a stent made of stainless steel. The pattern is similar to the pattern of FIGS. 3 and 4, and the same reference numerals are used to indicate the generally corresponding parts. The stents of the embodiment of FIGS. 5 and 6 will normally be expanded by a balloon, in conventional fashion.

The embodiments of FIGS. 3 and 5 can also be viewed as being made up of high frequency and low frequency vertical sinusoidal patterns or vertical loop containing sections which are arranged generally in the circumferential direction and which are periodically interconnected. Thus, there is a first loop containing section with loops occurring at a first frequency extending along line 301 and a second loop containing section with also occurring at said first frequency extending along line 302. A third loop containing section 303 extending along line 305 has loops occurring at a second frequency that is higher than said first frequency. It is disposed between the first and second loop containing sections and alternately joined to the first and second loop containing sections. In the illustrated embodiment, the high frequency is in a ratio of 3/2 to the low frequency. As noted above, the higher frequency loop containing elements are smaller in width. The relative widths can be selected so that the high frequency elements are crimpable to the same diameter as the lower frequency elements. A stent according to claim 4, wherein the higher frequency elements provide improved flexibility.

Furthermore the high frequency vertical patterns of smaller width result in elements having a lower maximal strain. Specifically, the lower maximal strain is below the maximum strain without non-elastic deformation for the material of the stent. In this embodiment where the stent is made of stainless steel the lower maximal strain is below approximately 0.4%, even for a 150° bend, as confirmed by finite element analysis. On the other hand, in a '303 type stent, for an equivalent amount of bending, exhibits a maximum strain of 8%. Thus, although the increased flexibility of the stent of the present invention means that, in addition to conforming better to the curved lumen, it will bend with each beat of the heart. The strain during heart beat happens 8,000,000 times every year and cannot be much above elastic limit without the stent breaking. Since, embodiments of the present invention keep the strain below the limit means that the stent of the present invention can bend with the lumen as the heart beats, for many years without breaking.

Also in this embodiment of the invention, for example, the second loops 531 are made stronger by shortening the third and fourth members 507, 510. This helps assure that the second loops do not "flare out" during delivery of the stent through tortuous anatomy. This "flaring out" is not a concern with NiTi stents which are covered by a sheath during delivery.

Furthermore, the length of the members in this embodiment may be shorter than the length of the corresponding members in the embodiment illustrated in FIGS. 3 and 4. Typically, the amount of strain allowed in a self-expanding NiTi stent may be around 10%. In a stainless steel stent, the amount of strain allowed during the plastic deformation which take place, for example, during expansion, typically may be 20% or greater. Therefore, to facilitate stents made of NiTi and stents made of stainless steel expanding to comparable diameters, the members of the NiTi stent may be longer than the members of a stainless steel stent.

Figure 15:
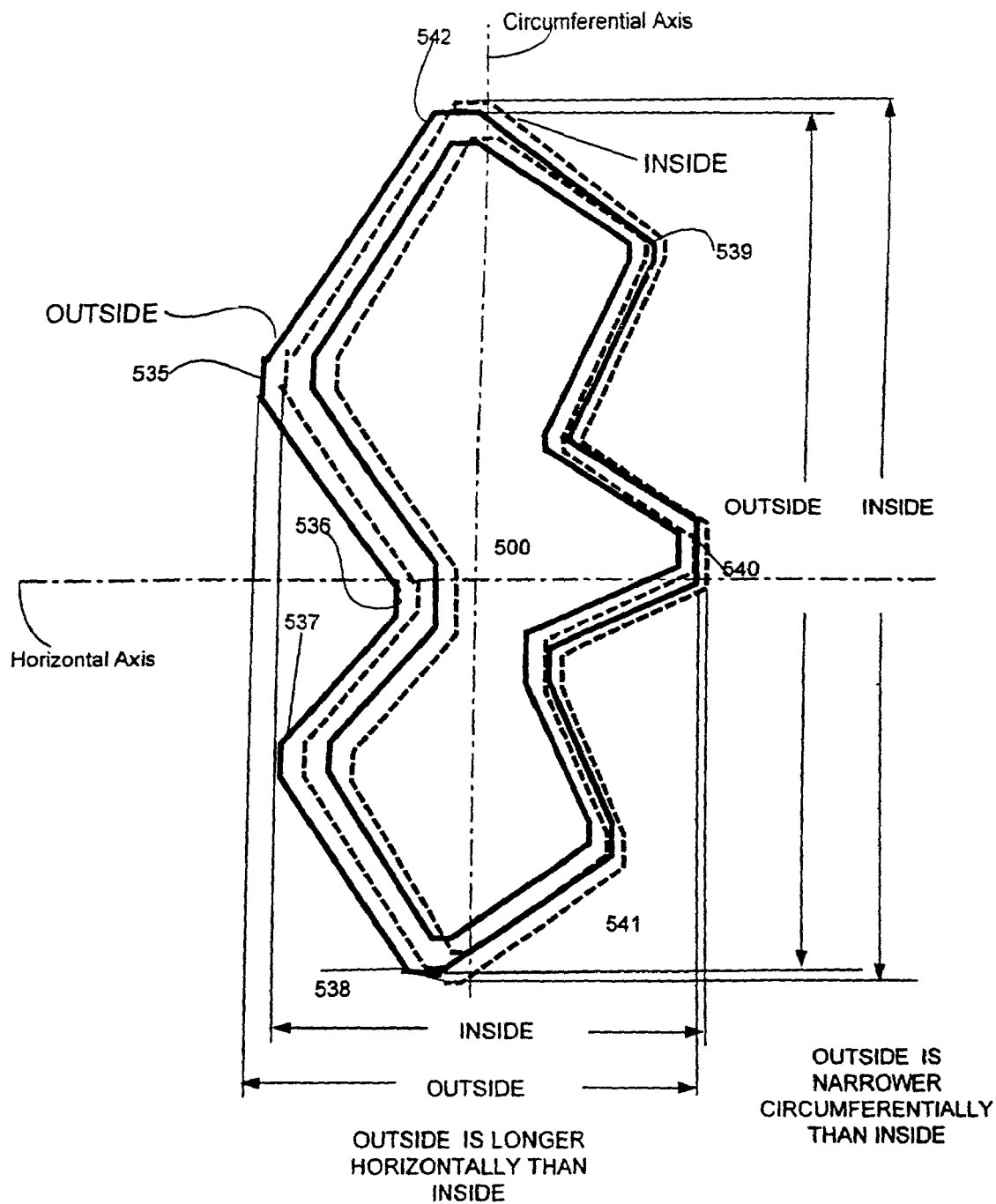
FIG. 15 shows a view of the shape of single cell on the outside of a curve superimposed on the same cell on the inside of a curve.

When the stent is within a curved lumen when it is expanded, the stent is curved as shown in FIG. 2 The result of this curving, for a single cell 500, is shown in FIG. 15. The cells on the outside of the curve open in length, but narrow in width whereas the cells on the inside of the curve shorten in length but thicken in width. As a result, the density of the members per unit of surface area remains closer to what it is in an uncurved, expanded condition, both on the inside and outside of the curve. Similarly, as can be seen from FIG. 15, the area of the cell remains more constant than it would without compensation. This results in maintaining a more constant density of stent elements in contact with the lumen, irrespective of location on the inside or outside of a curved section. In turn, when the stent is coated with a medicine, a more even dose is applied to the inside wall of the lumen, avoiding the possibility that a toxic dose be supplied at one area while a less than effective dose is applied to another area. In some cases, the ratio between a toxic dose and an effective dose may be smaller than 10:1.

Specifically, it can be appreciated that, in cells on the outside of the curve at the connection points 542 and 538, the cell will open up increasing the length of the cell. In addition, at the junction points 535, 536, 537, 539, 540 and 542, the adjoining struts will come closer to each other, to cause the cell to become narrower in width, or in the circumferential direction, compensating for the increase in length. On the inside of the curve, the longitudinal distances must decrease. Again, it is easy to see that the compression which occurs on the inside results in the struts on either side of the junction points 542 and 538 being squeezed closed and the width of the cell decreasing. At the same time, at the junction points 535, 536, 537, 539, 540 and 542, the struts will move further apart from each other and the cell becomes more narrow in length but thicker in width again providing compensation. Thus, in both cases, the increase in one direction is compensated in the other direction to make the area more constant than it would have been without the compensation.

FIG. 7 illustrates another aspect of the present invention. The stent of FIG. 7 is also constructed from orthogonal meander patterns 301, 302. The meander patterns form a series of interlocking cells 50, 700 of two types. The first type of cell 50 is taught by U.S. Pat. No. 5,733,303. These cells are arranged so that they form alternating bands 704 of first type of cells 50 and bands 706 of the second type of cells 700.

Figure 8:
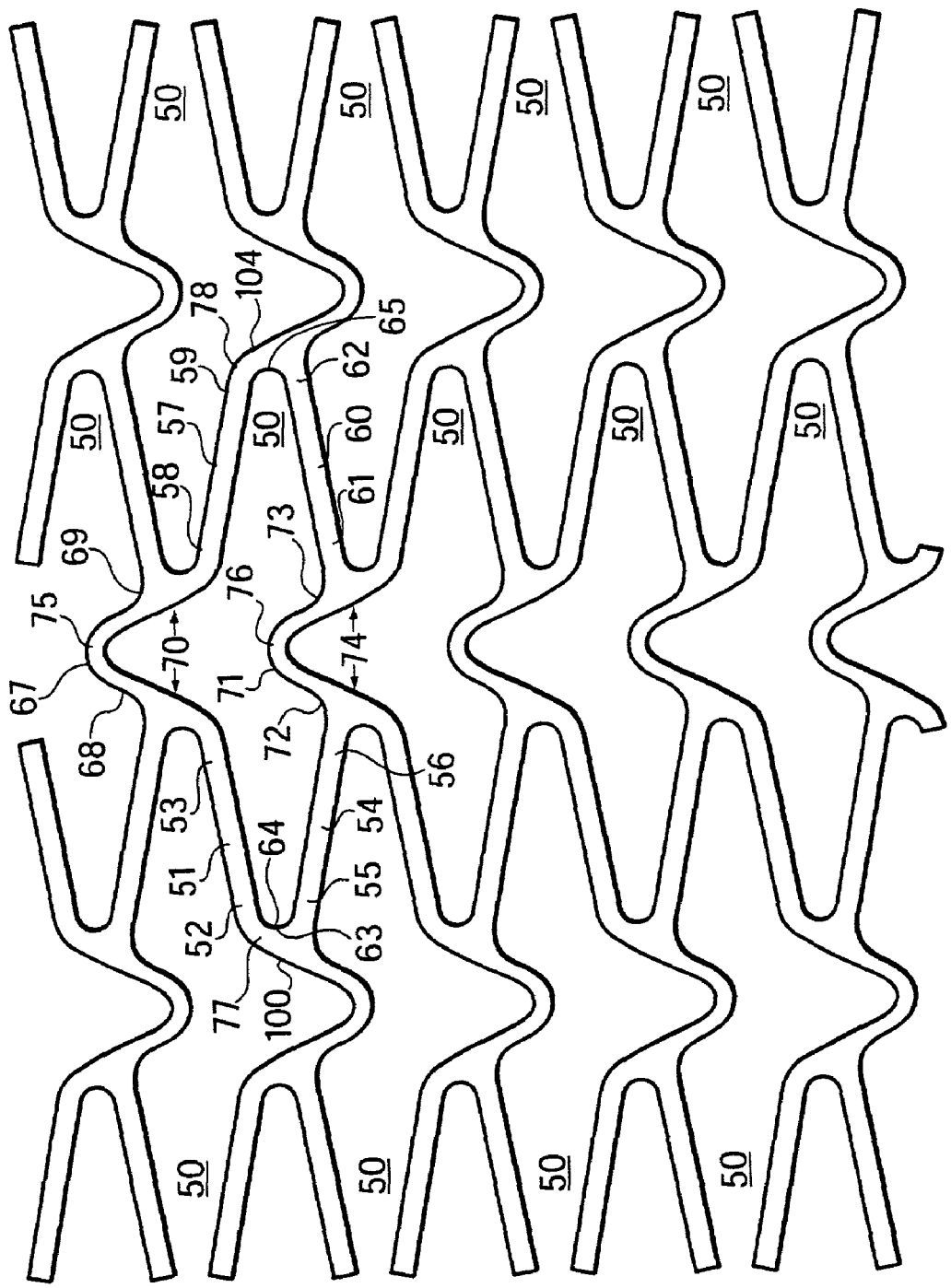
FIG. 8 shows an enlarged view of one cell used in the pattern of FIG. 7.

As seen in FIG. 8 and particularly with respect to the cell labeled for ease of description, each of the '303 cells 50 has a first longitudinal apex 100 and a second longitudinal end 78. Each cell 50 also is provided with a first longitudinal end 77 and a second longitudinal apex 104 disposed at the second longitudinal end 78. Each cell 50 also includes a first member 51 having a longitudinal component having a first end 52 and a second end 53; a second member 54 having a longitudinal component having a first end 55 and a second end 56; a third member 57 having a longitudinal component having a first end 58 and a second end 59; and a fourth member 60 having a longitudinal component having a first end 61 and a second end 62. The stent also includes a first loop or curved member 63 defining a first angle 64 disposed between the first end 52 of the first member 51 and the first end 55 of the second member 54. A second loop or curved member 65 defining a second angle 66 is disposed between the second end 59 of the third member 57 and the second end 62 of the fourth member 60 and is disposed generally opposite to the first loop 63. A first flexible compensating member (or a section of a longitudinal meander pattern) 67 having curved portion and two legs with a first end 68 and a second end 69 is disposed between the first member 51 and the third member 57 with the first end 68 of the first flexible compensating member 67 joined to and communicating with the second end 53 of the first member 51 and the second end 69 of the first flexible compensating member 67 joined to and communicating with the first end 58 of the third member 57. The first end 68 and the second end 69 are disposed a variable longitudinal distance 70 from each other. A second flexible compensating member (or, a section of a longitudinal meander pattern) 71 having a first end 72 and a second end 73 is disposed between the second member 54 and the fourth member 60. The first end 72 of the second flexible compensating member 71 is joined to and communicates with the second end 56 of the second member 54 and the second end 73 of the second flexible compensating member 71 is joined to and communicates with the first end 61 of the fourth member 60. The first end 72 and the second end 73 are disposed a variable longitudinal distance 74 from each other. In this embodiment, the first and second flexible compensating members, and particularly the curved portion thereof, 67 and 71 are arcuate.

When curved stent is expanded while inside a lumen, also in the case of the cells 50, cells on the outside of the curve open in length, but narrow in width whereas the cells on the inside of the curve shorten in length but thicken in width to provide a density of the members per unit of surface area that remains more constant between the inside and outside of the curve.

Specifically, it can be appreciated that, in cells on the outside of the curve the flexible connecting members 67 and 71 will open up increasing the distances 70 and 74. In addition, the members 57 and 60 will come closer to each other, as will members 51 and 54. This will further lengthen the cell. But at the same time it will become narrower in width, or in the circumferential direction to compensate for the opening up of the flexible connector members 67 and 71. On the inside of the curve, the longitudinal distances must decrease. Again, if is easy to see that the compression which occurs on the inside results in the loops 67 and 71 being squeezed closed and the distances 70 and 74 decreasing. At the same time, the members 57 and 60 and members 51 and 54 will move further apart from each other and the longitudinal components of members 57, 60, 51 and 54 will decrease. Thus, the cell becomes narrower in length but thicker in width. Thus, in both cases, the increase in one direction is compensated in the other direction to make the area more constant than it would have been without the compensation.

Figure 9:
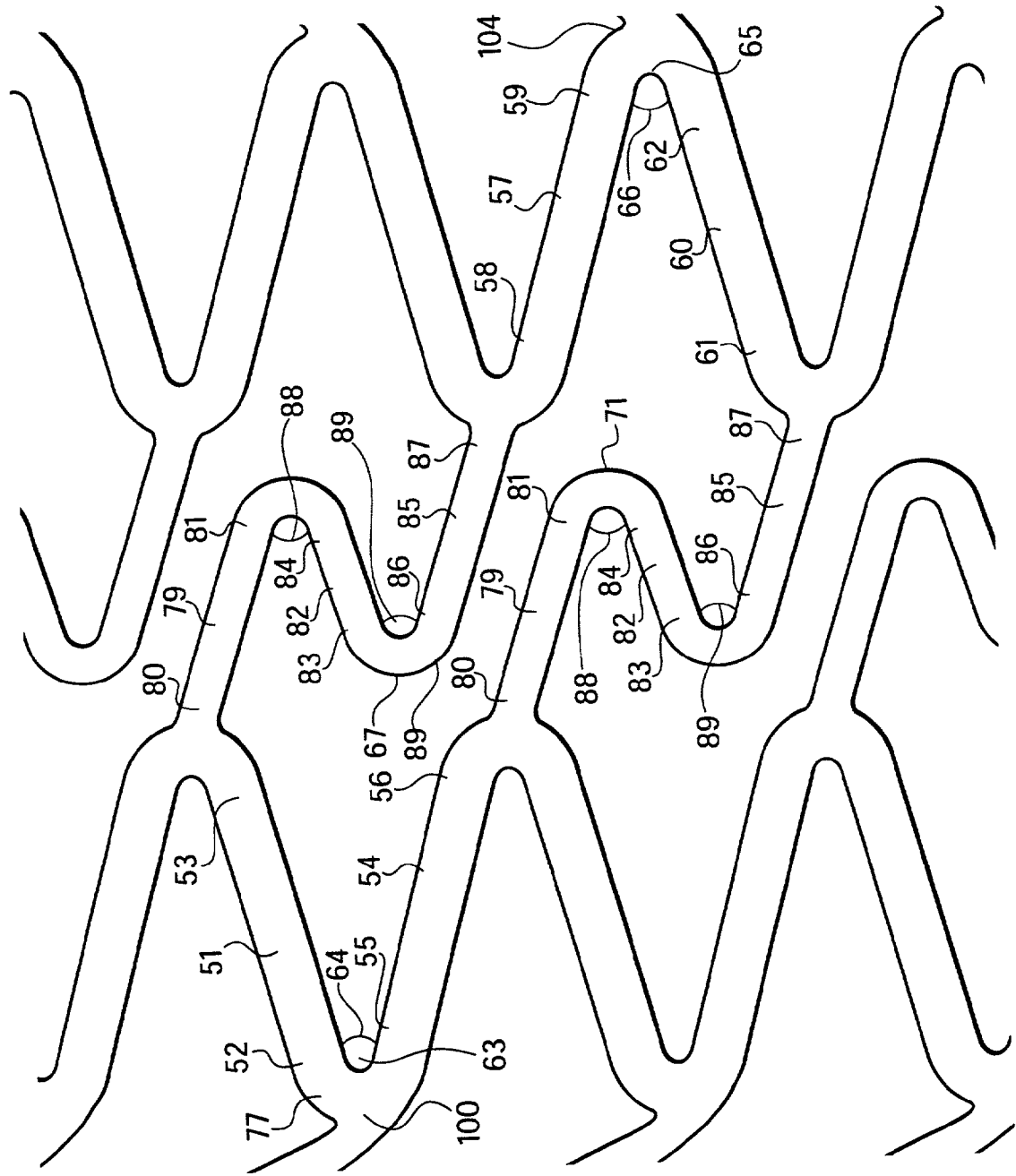
FIG. 9 shows an enlarged view of another cell used in FIG. 7.

The second type of cell 700 is illustrated in FIG. 9 and the same reference numerals are used to indicate generally corresponding areas of the cell. The apices 100, 104 of the second type of cell 700 are offset circumferentially. Also, each flexible compensating member 67, 71 includes: a first portion or leg 79 with a first end 80 and a second end 81; a second portion or leg 82 with a first end 83 and a second end 84; and a third portion or leg 85 with the first end 86 and a second end 87, with the second end 81 and the second end 84 being joined by a curved member and the first end 83 and the first end 86 being joined by a curved member. The first end of a flexible compensating member 67, 71 is the same as the first end 80 of the first portion 79, and the second end of a flexible compensating member 67, 71 is the same as the second end 87 of the third portion 85. A first area of inflection 88 is disposed between the second end 81 of the first portion 79 and the second end 84 of the second portion 82 where the curved portion joining them lies. A second area of inflection 89 is disposed between the first end 83 of the second portion 82 and the first end 86 of the third portion 85 where the curved portion joining them lies.

While FIG. 7 illustrates a pattern of alternating bands of cells, the stent may be optimized for a particular usage by tailoring the configuration of the bands. For example, the middle band of the second type of cells 700 may instead be formed of cells 50, or vice versa. The second type of cells in FIG. 7 may also utilize the cell configurations described with respect to FIGS. 4 and 6. The cell configurations of FIGS. 4 and 6 provide the advantage that they will not cause any torque of one portion of the cell relative to another portion of the cell about the longitudinal axis of the stent upon expansion, which may happen when the second type of cells 700 expand, a torque which could cause a stent to deform, and stick out.

As illustrated in FIG. 7, all of the flexible compensating members are arranged so that the path of the flexible compensating members, from left to right, travels in a generally downward direction. The cells 700 can also be arranged so that the flexible compensating members in one band are arranged in a generally upward direction, and the flexible compensating members in an adjacent band are arranged in a generally downward direction. One skilled in the art can easily make these modifications.

Figure 10:
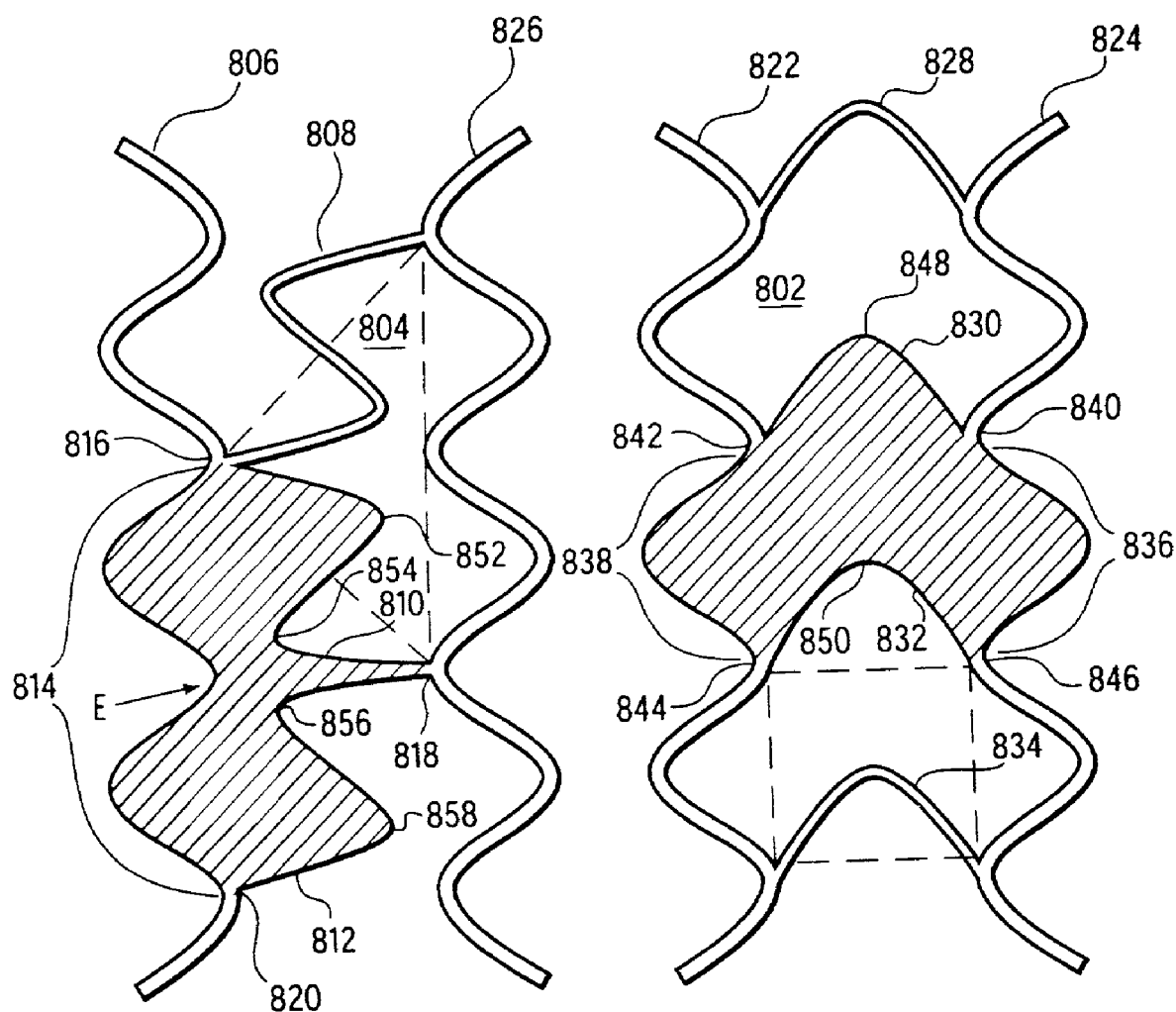
FIG. 10 shows a schematic comparison of a four cornered or "square cell" and a three cornered or "triangular" cell of the present invention.

FIG. 10 is a schematic representation comparing the cells 804 of the present invention, which have three points where the intertwined first and second meander patterns meet and are in that sense three cornered or triangular cells, with cells 802 of the '303 stent which have four points where the intertwined first and second meander patterns meet and are in that sense four cornered or square cells. More particularly, on the left side of FIG. 10, a pair of vertical meander patterns 806, 826 are joined by members 808, 810, 812 (which are sections of longitudinal meander patterns) to form a plurality of three cornered or triangular cells 804. By triangular cell, it is meant that there are three sections 810, 812, 814, each having loop portions and three associated points 816, 818, 820 of their joining, forming each cell.

On the right side of FIG. 10, a pair of vertical meander patterns 822, 824 are joined together compensating members 828, 830, 832, 834 (which are sections of a longitudinal meander) to form a plurality of square cells 804. By square cell, it is meant that there are four sections, each having loop portions, and four associated points of their joining, forming each cell. For example, the shaded cell 802 is formed from four sections 832, 836, 830, 838, with four associated points of their joining 840, 842, 844, 846.

Both the square cell and the triangular cell have two kinds of sections with loops. The first kind of loop containing section is formed from a vertical meander pattern and is optimized predominantly to enable radial support. The second kind of loop containing section is optimized predominantly to enable flexibility along the longitudinal axis of the stent. Although each loop containing section is optimized predominantly to enable a desired characteristic of the stent, the sections are interconnected and cooperate to define the characteristics of the stent. Therefore, the first kind of loop containing section contributes to the longitudinal flexibility of the stent, and the second kind of loop containing section contributes to the radial support of the stent.

In the square cell 802, it can be seen that the second kind of loop containing sections 830, 832 each have one inflection point 848, 850. In the triangular cell, the loop containing sections 810, 812 each have two inflection point areas 852, 854, 856, 858. The higher number of inflection points allows more freedom to deform after expansion of the stent and distributes the deformation over a longer section, thus, reducing the maximal strain along these loop containing sections.

Furthermore, it can be seen that a square cell 802 is generally more elongated along the longitudinal axis of the stent than a triangular cell 804, which is generally more elongated along the circumference of the stent. This also contributes to higher flexibility after expansion.

If the first meander patterns 806, 822, 824, 826 of both types of cells are constructed identically and spaced apart by the same amount, the area of a triangular cell 804 is the same as a square cell 802. This can be more readily understood with reference to a band of cells around the circumference of a stent. Each band will encompass the same area, and each band will have the same number of cells. Accordingly, the area of each cell in one band formed of square cells will be the same as the area of each cell in another band formed of triangular cells.

Although the areas of the cells are equal, the perimeter of the triangular cell is larger than the perimeter of the square cell. Therefore, in comparison to a square cell, a triangular cell offers increased coverage of a vessel wall.

Figure 11:
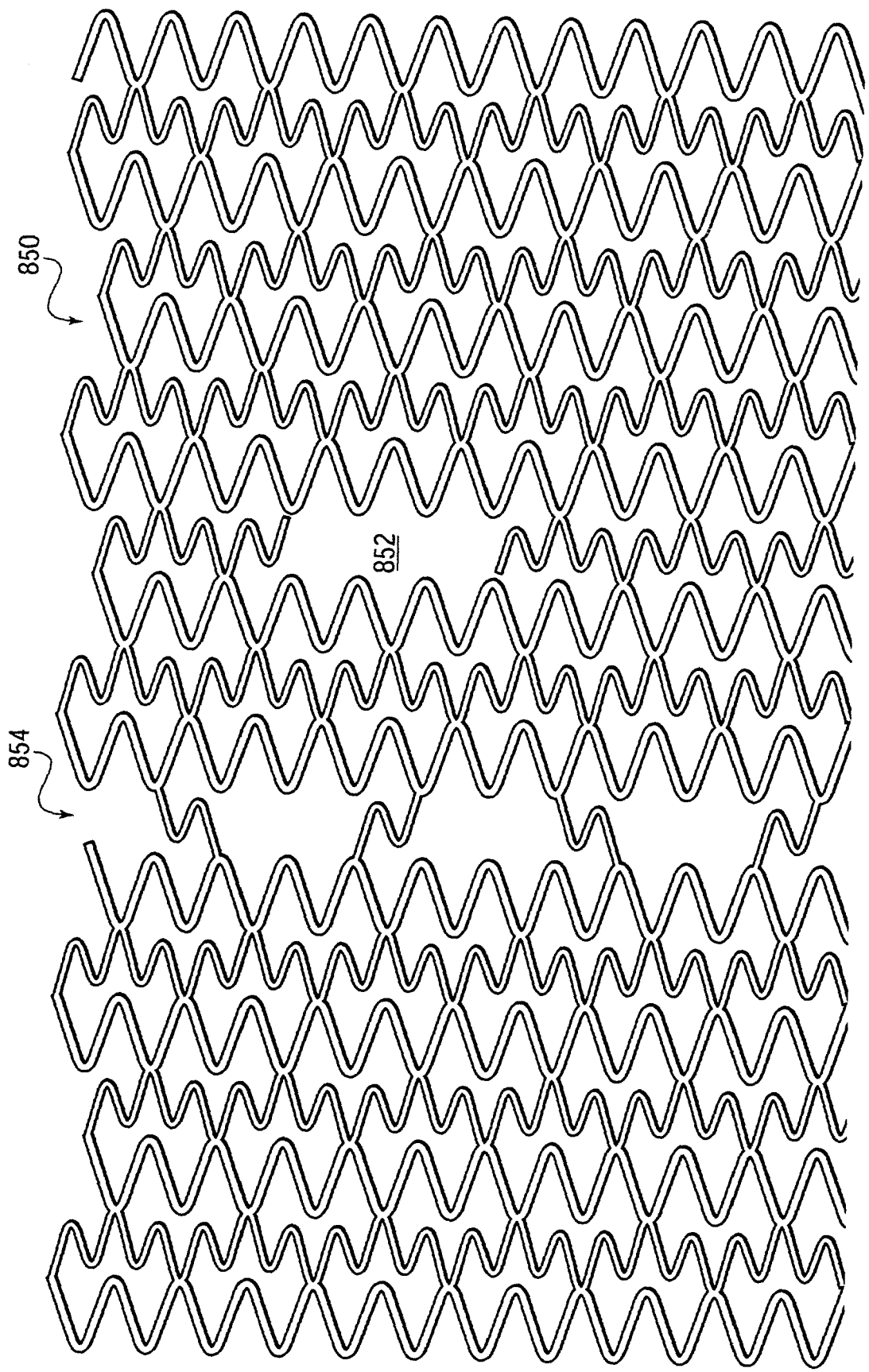
FIG. 11 shows a pattern for a stent constructed according to the principles of the invention which has variable geometry along its length.

In the particular embodiments described above, the stent is substantially uniform over its entire length. However, other applications where portions of the stent are adapted to provide different characteristics are also possible. For example, as shown in FIG. 11, a band of cells 850 may be designed to provide different flexibility characteristics or different radial compression characteristics than the remaining bands of cells by altering the widths and lengths of the members making up that band. Or, the stent may be adapted to provide increased access to a side branch lumen by providing at least one cell 852 which is larger in size then the remaining cells, or by providing an entire band of cells 854 which are larger in size than the other bands of cells. Or, the stent may be designed to expand to different diameters along the length of the stent. The stent may also be treated after formation of the stent by coating the stent with a medicine, plating the stent with a protective material, plating the stent with a radiopaque material, or covering the stent with a material.

Figure 12:
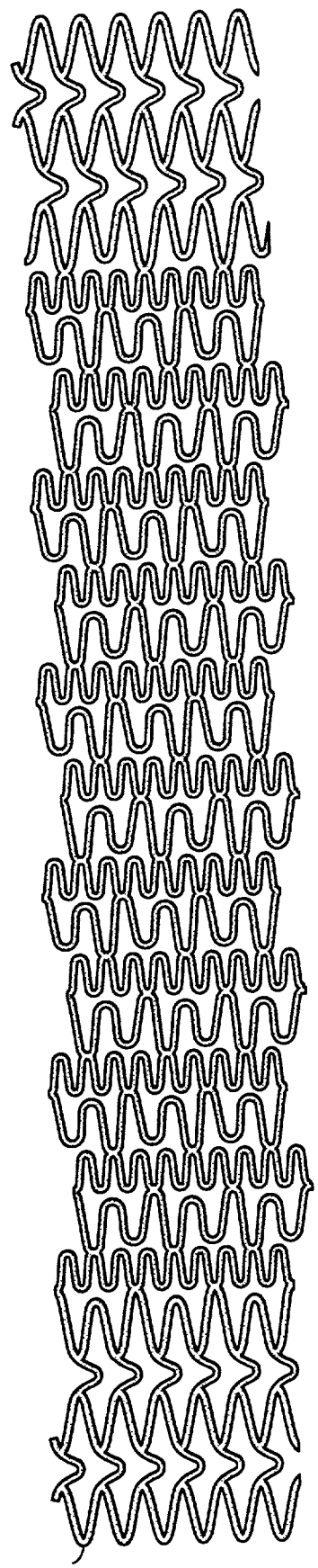
FIG. 12 shows another pattern for a stent constructed according to the principles of the invention.
Figure 13:
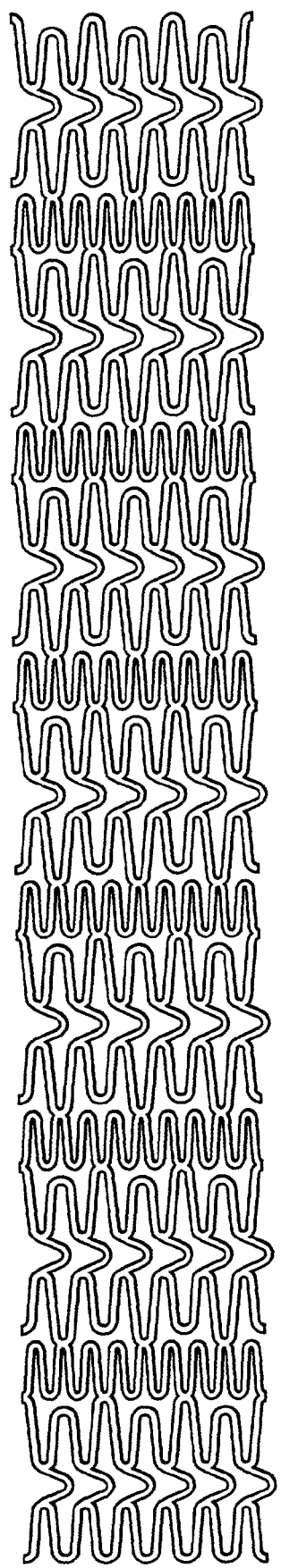
FIG. 13 shows another pattern for a stent constructed according to the principles of the invention.

FIGS. 12 and 13 show alternative patterns for a stent constructed according to the principles of the present invention. The stent shown in FIG. 12 has two bands of cells 856 located at each of the proximal end 860 and distal and 862. The cells that form the bands of cells 856 located at the ends of the stent are '303 type cells. The remaining cells in the stent are the same as described with respect to the cells 500 depicted in FIG. 6. The stent shown in FIG. 13 has alternating bands of cells 864, 866, 868. The first type of band of cells 864 is composed of '303 type cells. The second and third types of bands of cells 866, 868 are formed of the cells described with respect to the cells 500 depicted in FIG. 4. Of course, any various combination of cells may be used in the present invention.

Thus, what is described is a longitudinally flexible stent that utilizes a closed cell structure to provide excellent coverage of the vessel wall. The general concepts described herein can be utilized to form stents with different configurations than the particular embodiments described herein. For example, the general concepts can be used to form bifurcated stents. It will be appreciated by persons skilled in the art that the present invention is not limited to what has been particularly shown and described above. Rather, the scope of the present invention is defined by the claims which follow.

What is claimed is:

1. A coronary stent having a longitudinal axis along the length of the stent comprising:
   a. a first loop containing section having loops, said first loop containing section having an axis orthogonal to the longitudinal axis of the stent, the loops in said first loop containing section occurring at a first frequency;
   b. a second loop containing section having loops, said second loop containing section having an axis orthogonal to the longitudinal axis of the stent, the loops in said second loop containing section also occurring at said first frequency;
   c. said first and second loop containing sections each form a single, continuous, generally sinusoidal pattern around the entire circumference of the stent; and
   d. a third loop containing section, said third loop containing section formed of a single, continuous, generally sinusoidal pattern also having an axis orthogonal to the longitudinal axis of the stent, the loops in said third loop containing section occurring at a second frequency that is higher than said first frequency, said third loop containing section disposed in the general circumferential space between each of said first and second loop containing sections to form consecutive repeating patterns along the longitudinal axis of the stent for at least two repetitions and alternately joined to said first and second loop containing sections directly at curved portions of said first, second and third loop containing sections forming a uniform pattern of flexible cells;
   e. the loops in said first, second and third loop containing sections being disposed and adapted to cooperate so that, components of said third loop containing section contribute to the cell's elongating or shortening when the stent is flexed; and
   f. the loops of the first, second, and third loop containing sections further include struts having a thickness in the radial direction and width in the circumferential direction, wherein the struts of the first and second loop containing sections are wider than the width of the struts of the third loop containing section.

2. A stent according to claim 1, wherein the loops in the first loop containing sections are all in phase.

3. A stent according to claim 1, wherein, upon expansion, the cells on the outside of a curved section of the stent narrows as the cells elongate, and cells inside of a curve widen as the cells shorten.

4. A coronary stent comprising:
   a. a first circumferential band, formed of a single, continuous, generally sinusoidal pattern of loops at a first frequency having a single axis extending around the entire circumference of the stent;
   b. a second circumferential band, formed of a single, continuous, generally sinusoidal pattern of loops, said second band having an axis parallel to the axis of the first band, and said loops occurring at a second frequency higher than said first frequency, said second circumferential band extending in a continuous pattern of loops around the entire circumference of the stent, said first circumferential band alternating with said second circumferential band to form consecutive patterns along the longitudinal axis of the stent for at least two repetitions, said second bands periodically coupled to said first bands directly at curved portions of said first and second circumferential bands to form cells;

c. patterns of loops in said bands being disposed and adapted to cooperate so that second circumferential bands contribute more than first circumferential bands to deformation during flexing of the stent; and d. the loops of the first, and second bands further include struts having a thickness in the radial direction and width in the circumferential direction, wherein the struts of the first bands are wider than the width of the struts of the second bands.

5. A stent according to claim 4, wherein, upon expansion, the cells on the outside of a curved section of the stent narrows as the cells elongate, and cells inside of a curve widen as the cells shorten.

6. A coronary stent having a longitudinal axis along the length of the stent consisting essentially of in both the unexpanded and expanded state:

a. a first loop containing section, said first loop containing section having an axis perpendicular to the longitudinal axis of the stent, the loops in said first loop containing section occurring at a first frequency;

b. a second loop containing section, said second loop containing section having an axis perpendicular to the longitudinal axis of the stent, the loops in said second loop containing section also occurring at said first frequency, said second loop containing section being 180° out of phase with said first loop containing section along the longitudinal axis of the stent;

c. at least one of said first and second loop containing sections formed of a single, continuous, generally sinusoidal pattern; and d. a third loop containing section, said third loop containing section formed of a single, continuous, generally sinusoidal pattern extending in a continuous band of loops around the entire circumference of the stent, the loops in said third loop containing section occurring at a second frequency that is higher than said first frequency, said loops in said third loop containing section having an axis parallel to the axis of the first and second loop containing sections, said third loop containing section disposed in the generally circumferential space between each of said first and second loop containing sections to form consecutively repeating patterns along the longitudinal axis of the stent for at least two repetitions and alternately joined to said first and second loop containing sections, said first, second and third loop containing sections forming a pattern of uniform cells; and e. the loops of the first, second, and third loop containing sections further include struts having a thickness in the radial direction and width in the circumferential direction, wherein the struts of the first and second loop containing sections are wider than the struts of the third loop containing section.

* * * * *